US00PP30771P2

(12) United States Plant Patent
Kievit

(10) Patent No.: US PP30,771 P2
(45) Date of Patent: Jul. 30, 2019

(54) ***HELENIUM* PLANT NAMED 'BALSALULOW'**

(50) Latin Name: *Helenium autumnale*
Varietal Denomination: Balsalulow

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/999,955

(22) Filed: Sep. 4, 2018

(51) Int. Cl.
*A01H 5/02* (2018.01)
*A01H 6/14* (2018.01)

(52) U.S. Cl.
USPC ..... Plt./435
CPC ..... *A01H 6/14* (2018.05); *A01H 5/02* (2013.01)

(58) Field of Classification Search
USPC ..... Plt./435
CPC ..... A01H 5/02
See application file for complete search history.

(56) References Cited

PUBLICATIONS http://hardyplugs.com/gul.htm; Jul. 11, 2018; 32 pages.*
https://www.ballseed.com/PlantInfo/?phid=031608483006060; Mar. 28, 2019; 4 pages.*

* cited by examiner

*Primary Examiner* — Kent L Bell
(74) *Attorney, Agent, or Firm* — Audrey Charles

(57) ABSTRACT

A new and distinct cultivar of *Helenium* plant named 'Balsalulow', characterized by its medium yellow-colored inflorescences, medium green-colored foliage, and moderately vigorous, and compact-upright growth habit, is disclosed.

1 Drawing Sheet

Latin name of genus and species of plant claimed: *Helenium autumnale.*

Variety denomination: 'Balsalulow'.

BACKGROUND OF THE INVENTION

The present invention relates to a new and distinct cultivar of *Helenium* plant botanically known as *Helenium autumnale* and hereinafter referred to by the cultivar name 'Balsalulow'.

The new cultivar originated in a controlled breeding program in Hem, The Netherlands during August 2012. The objective of the breeding program was the development of *Helenium* cultivars having increased branching and a compact growth habit.

The new *Helenium* cultivar is the result of open-pollination within an insect-cage environment of six proprietary *Helenium autumnale* breeding selections not coded, not patented, characterized by varying shades of yellow, medium green-colored foliage, and moderately vigorous, upright growth habit. The new cultivar was discovered and selected as a single flowering plant within the progeny of the above stated open-pollination during July 2014 in a controlled environment in Hem, The Netherlands.

Asexual reproduction of the new cultivar by terminal stem cuttings since July 2014 in Hem, The Netherlands and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsalulow' as a new and distinct cultivar of *Helenium* plant:

1. Medium yellow-colored inflorescences;
2. Medium green-colored foliage;
3. Moderately vigorous, and compact-upright growth habit.

Plants of the new cultivar differ from plants of the parents primarily in having a more compact growth habit.

Of the many commercially available *Helenium* cultivars, the most similar in comparison to the new cultivar is MARIACHI 'Sombrero', U.S. Plant Pat. No. 25,968. However, in side by side comparisons, plants of the new cultivar differ from plants of 'Sombrero' in at least the following characteristics:

1. Plants of the new cultivar have a ray floret color slightly different from plants of 'Sombrero';
2. Plants of the new cultivar have narrower ray florets than plants of 'Sombrero'; and
3. Plants of the new cultivar have smaller diameter inflorescences than plants of 'Sombrero'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balsalulow'. The plants were approximately four months old. The plants were grown in one-gallon containers for approximately 11 weeks in a greenhouse in Elburn, Ill. Plants were given two pinches, one at one week before transplant and one two weeks after transplant.

DETAILED BOTANICAL DESCRIPTION

Figure 1:
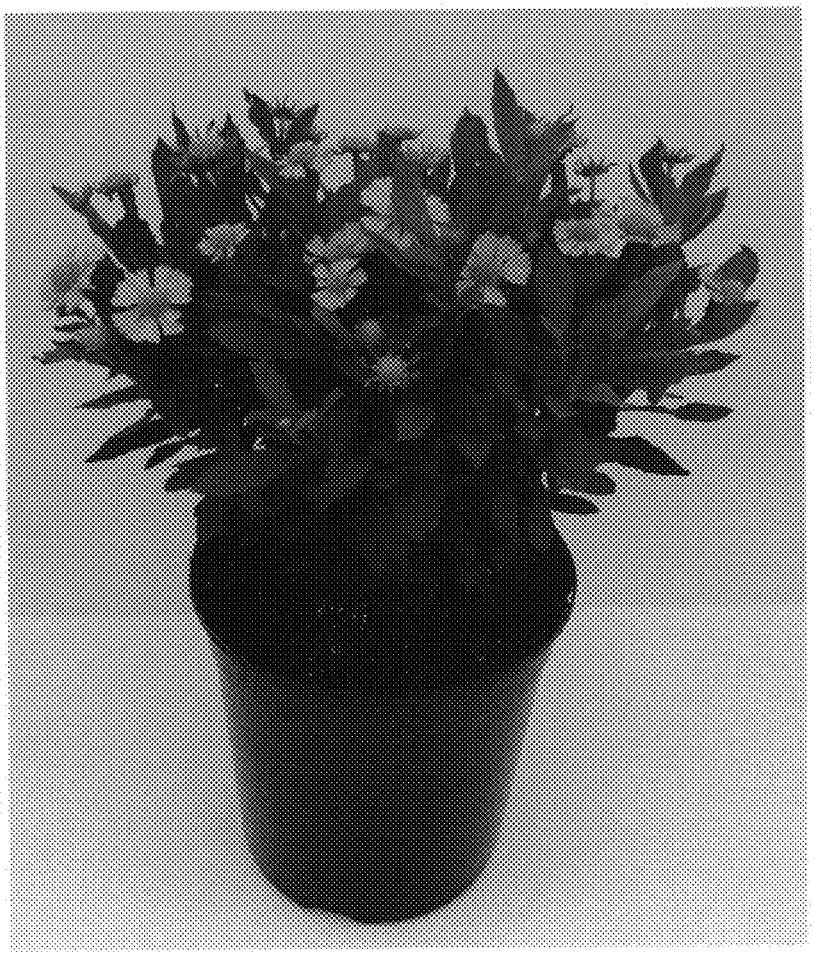
FIG. 1 illustrates a side view of the overall growth and flowering habit of 'Balsalulow'.
Figure 2:
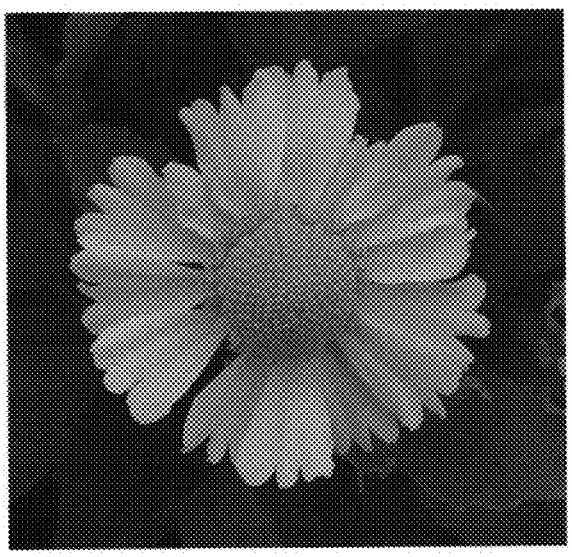
FIG. 2 illustrates a close-up view of an individual inflorescence of 'Balsalulow'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2018 under natural light conditions in West Chicago, Ill.

The following descriptions and measurements describe approximately six-month old plants produced from cuttings from stock plants and grown under conditions comparable to those used in commercial practice. The plants were grown in one-gallon containers for approximately 11 weeks in a greenhouse in Elburn, Ill. followed by 7 weeks in an open-sided polyhouse in West Chicago, Ill. Plants were given two pinches, one at one week before transplant and one two weeks after transplant. Greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Helenium autumnale* 'Balsalulow'.

Parentage:

*Female and male parents*.—Six proprietary *Helenium autumnale* breeding selections not coded, not patented.

Propagation:

*Type cutting*.—Terminal stem.

*Time to initiate roots*.—Approximately 10 to 12 days at 70° F. (21° C.).

*Time to produce a rooted cutting*.—Approximately 6 to 7 weeks at 70° F. (21° C.).

*Root description*.—Fibrous, medium to thin in thickness.

*Rooting habit*.—Freely branching, dense.

Plant description:

*Commercial crop time*.—Approximately 10 to 12 weeks from a rooted cutting to finish in a 15 cm container.

*Growth habit and general appearance*.—Herbaceous perennial, moderately vigorous, and compact-upright, vernalization not required for flowering.

*Hardiness*.—USDA Zone 4a (−30° F. to −25° F./−34.4° C. to −31.7° C.).

*Size*.—Height from soil level to top of plant plane: Approximately 30.0 cm. Width: Approximately 41.5 cm.

*Branching habit*.—Freely branching, pinching improves lateral branching. Quantity of main branches per plant: Approximately 9.

*Stems*.—Strength: Strong. Aspect: Erect to 45° angle. Shape: Mostly rounded with ridges from excurrent leaves. Length to base of inflorescence: Approximately 24.0 cm. Diameter: Approximately 3.0 mm to 6.0 mm. Length of central internode: Approximately 1.5 cm. Texture: Sparsely pubescent. Color of young stems: 146D. Color of mature stems: 146C sometimes tinted with 187A, becoming woody 200B with age.

Foliage description:

*General description*.—Form: Simple. Arrangement: Alternate.

*Leaves*.—Aspect: Acute to perpendicular to stem. Shape: Oblanceolate. Margin: Shallowly serrate. Apex: Acute. Base: Excurrent to stem. Venation pattern: Pinnate. Length of mature leaf: Approximately 5.3 cm with excurrent portion of approximately 1.0 cm to 2.0 cm in lower node. Width of mature leaf: Approximately 1.4 cm. Texture of upper and lower surfaces: Moderately pubescent with short hairs. Color of upper surface of young and mature foliage: NN137A with midvein of 147C. Color of lower surface of young and mature foliage: Closest to 137B with midvein of 147C.

Flowering description:

*Flowering habit*.—'Balsalulow' is a long day obligate, freely flowering under outdoor growing conditions blooming from summer through autumn.

*Lastingness of individual inflorescence on the plant*.—Approximately 3 to 4 weeks.

Inflorescence description:

*General description*.—Type: Solitary, composite. Persistent. Shape: Radiant head. Aspect: Facing upward. Arrangement: Terminal, held upright on strong peduncles. Fragrance: None detected. Quantity per plant: Approximately 38. Diameter: Approximately 3.0 cm. Depth: Approximately 1.0 cm.

*Peduncle*.—Strength: Strong. Aspect: Erect to approximately 45° from vertical. Length: Approximately 2.5 cm. Diameter: Approximately 2.0 mm. Texture: Densely pubescent with short appressed hairs. Color: 146B.

*Bud*.—Quantity per plant: Approximately 15. Shape: Globose becoming dome- shaped. Diameter: Approximately 1.0 cm. Depth: Approximately 5.0 mm. Color: 151A.

*Ray florets*.—Quantity per inflorescence: Approximately 15, occasionally with one or two being underdeveloped. Arrangement: In a single whorl, slightly imbricate. Aspect: Perpendicular to disc, subtending with age. Shape: Obdeltoid, fan-like. Appearance: Dull. Margin: Entire. Apex: Three to four lobed. Base: Attenuate. Length: Approximately 1.3 cm. Width: Approximately 7.0 mm. Texture of upper surface: Glabrous. Texture of lower surface: Densely pubescent, slightly longitudinally ribbed. Color of upper surface when first open: 13A. Color of lower surface when first open: 13B. Color of upper surface when fully open: 13B. Color of lower surface when fully open: 13C.

*Disc florets*.—Disc diameter: Approximately 1.3 cm. Quantity per inflorescence: Approximately 150.

Arrangement: Spirally arranged in center of inflorescence. Shape: Tubular. Margin of free portion: Entire. Apex: Five acute tips. Base: Fused into a tube. Length: Approximately 4.0 mm. Diameter: Approximately 1.0 mm. Texture of inner surface: Glabrous. Texture of outer surface: Glabrous with densely pubescent base. Color of upper or inner surface when first and fully open: 13B. Color of lower or outer surface when first and fully open: 13A, base of 155D.

*Receptacle*.—Shape: Conical. Height: Approximately 3.0 mm. Diameter: Approximately 4.0 mm. Color: 155D.

*Phyllaries*.—Quantity per inflorescence Approximately 15. Arrangement: In a single whorl. Appearance: Dull. Shape: Lanceolate. Margin: Entire. Apex: Acute. Base: Truncate. Length: Approximately 8.0 mm. Width: Approximately 1.0 mm. Texture of upper or inner surface: Glabrous. Texture of lower or outer surface: Densely pubescent with short hairs. Color of upper surface: 146B. Color of lower surface: 146C.

*Reproductive organs*.—Androecium: Present on disc florets only. Stamen quantity: 5 per floret. Anther shape: Oblong, basifixed. Anther length: Approximately 1.5 mm. Anther color: 13A. Filament length: Approximately 1.5 mm. Filament color: 13D. Pollen amount: Moderate. Pollen color: 13B. Gynoecium: Present on both disc and ray florets. Pistil quantity: 1 per floret. Pistil length: Approximately 4.0 mm. Stigma shape: Bifid. Stigma length: Approximately 0.5 mm. Stigma color: 13A. Style length: Approximately 2.5 mm. Style color: 13D. Ovary length: Approximately 1.0 mm. Ovary color: 155D.

Seed and fruit production: Neither seed nor fruit production has been observed.

Disease and pest resistance: Resistance to pathogens and pests common to *Helenium* has not been observed to date.

What is claimed is:

1. A new and distinct cultivar of *Helenium* plant named 'Balsalulow', substantially as herein illustrated and described.

* * * * *